US006552146B1

(12) United States Patent
Mougin

(10) Patent No.: US 6,552,146 B1
(45) Date of Patent: *Apr. 22, 2003

(54) COMPOSITION COMPRISING POLYMERS HAVING A STAR STRUCTURE, THE POLYMERS, AND THEIR USE

(75) Inventor: Nathalie Mougin, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/543,778

(22) Filed: Apr. 5, 2000

(30) Foreign Application Priority Data

Apr. 6, 1999 (FR) .............................. 99 04255

(51) Int. Cl.[7] .............................................. C08F 118/02
(52) U.S. Cl. .................... 526/319; 525/299; 525/305; 525/314; 528/183; 528/258; 528/263; 528/298; 528/303.1; 528/307.4; 528/310; 528/318.4; 528/331
(58) Field of Search ................... 526/258, 263, 526/298, 303.1, 307.2, 307.4, 307.6, 310, 317.1, 318, 318.4, 320, 328, 328.5, 319, 183; 525/293, 299, 314, 305

(56) References Cited

U.S. PATENT DOCUMENTS

| 3,907,984 A | | 9/1975 | Calvert et al. | |
|---|---|---|---|---|
| 4,659,783 A | * | 4/1987 | Spinelli ..................... | 525/293 |
| 5,221,534 A | | 6/1993 | DesLauriers et al. .... | 424/78.03 |
| 5,362,813 A | | 11/1994 | Antonelli et al. ........... | 525/286 |
| 5,371,147 A | | 12/1994 | Spinelli et al. | |
| 5,525,636 A | | 6/1996 | Henn et al. .................... | 521/59 |
| 5,527,524 A | | 6/1996 | Tomalia et al. ............. | 424/1.33 |
| 5,552,491 A | * | 9/1996 | Mishra et al. ............... | 525/299 |
| 5,804,664 A | | 9/1998 | Kennedy et al. | |
| 5,807,937 A | | 9/1998 | Matyjaszewski et al. ... | 526/135 |
| 5,849,278 A | | 12/1998 | Poit et al. ................... | 424/70.7 |
| 5,919,442 A | | 7/1999 | Yin et al. ................. | 424/78.18 |
| 5,986,020 A | | 11/1999 | Campbell et al. ............. | 526/64 |
| 6,001,342 A | | 12/1999 | Forestier et al. ........... | 424/76.1 |
| 6,013,735 A | * | 1/2000 | Mishra et al. ............... | 525/299 |
| 6,024,948 A | | 2/2000 | Samain et al. ........... | 424/70.16 |
| 6,090,902 A | | 7/2000 | Kuo et al. ................... | 526/279 |
| 6,113,882 A | | 9/2000 | Mougin eta l. ................ | 424/47 |
| 6,124,411 A | | 9/2000 | Matyjaszewski et al. ... | 526/111 |
| 6,132,736 A | | 10/2000 | Mellul et al. ............... | 424/401 |
| 6,150,468 A | | 11/2000 | Schoenberg et al. ........ | 525/222 |

FOREIGN PATENT DOCUMENTS

| DE | 43 28 004 | 2/1995 |
|---|---|---|
| DE | 196 02 540 | 7/1997 |
| EP | 0 557 196 | 8/1993 |
| EP | 0 639 371 | 2/1995 |
| EP | 0 704 477 | 4/1996 |
| WO | WO 86/00626 | 1/1986 |
| WO | WO 96/17886 | 6/1996 |
| WO | WO 96/36323 | 11/1996 |
| WO | WO 96/33690 | 10/1997 |

OTHER PUBLICATIONS

"Polymer Chemistry", second edition, 1988 Seymour et al, Mercel Dekker, Inc., pp. 354–358.*
"Polymer Handbook" third edition, 1972 John Willey and Sons, Brandrup et al p. II–193.*
English Language esp@cenet Abstract of EP 0557 196.
English Language esp@cenet Abstract of EP 0639 371.
English Language esp@cenet Abstract of WO 96/17886.
English Language esp@cenet Abstract of EP 0 704 477.
English language Derwent Abstract of DE 196 02 540.
English language Derwent Abstract of DE 43 28 004.
English language Derwent Abstract of DE196 05 540.

* cited by examiner

Primary Examiner—Tatyana Zalukaeva
(74) Attorney, Agent, or Firm—Finnegan, Henderson, Farabow, Garrett & Dunner, LLP

(57) ABSTRACT

A composition, comprising, in an appropriate medium, at least one polymer with a highly specific ordered structure is disclosed. These compositions find a specific application in the field of make-up and are capable of being applied to keratinous fibers, in particular to the nails, eyelashes, eyebrows and hair. In particular, these compositions can make it possible to obtain a film which exhibits good resistance to chipping, to impacts, to rubbing movements, to scratches and/or to pressing actions.

71 Claims, No Drawings

COMPOSITION COMPRISING POLYMERS HAVING A STAR STRUCTURE, THE POLYMERS, AND THEIR USE

The present invention relates to a composition, in particular a cosmetic or pharmaceutical composition, comprising, in an appropriate medium, at least one polymer with a highly specific ordered structure. These compositions find a specific application in the field of make-up and are capable of being applied to keratinous fibres, in particular to the nails, eyelashes, eyebrows and hair.

Compositions to be applied to keratinous fibres, such as nail varnishes or nail care bases, usually comprise a film-forming polymer in solution or dispersion in an organic or aqueous solvent, colouring materials, such as dyes or pigments, and generally plasticizers and rheological agents.

Mention is very particularly be made, among the main characteristics which nail varnishes should possess, of the absence of irritation of the skin and nails, ready application, a rapid drying time and the production of a homogeneous film which has excellent gloss.

Furthermore, there is also a search for compositions which result in the formation of a film which exhibits a degree of flexibility, indeed even of suppleness, leading to good resistance to chipping of the varnish, in particular in the case of impacts, and to the formation of sufficiently hard films (surface hardness) to moderate, indeed even avoid, wearing of the film in the case of rubbing movements.

It is therefore usual, in preparing nail varnishes, to employ film-forming materials, such as nitrocellulose, if preferred in combination with another polymer, such as an acrylic resin or an alkyd resin, and with plasticizers. The role of the plasticizers is to confer suppleness on the make-up film. This is because the use of a film-forming polymer alone generally gives a rigid, brittle and delicate film which rapidly wears away. However, the addition of a plasticizer can sometimes lead to other disadvantages, such as yellowing of the film, instability of the composition with regard to light and/or heat, lack of gloss and lack of fluidity.

Furthermore, the majority of compositions known to date exhibit the fault of rapidly wearing away at the surface, which obliges the user to renew, at very frequent time intervals, the application of a fresh layer of varnish after removing the damaged layer. It may be noted that the solutions provided for overcoming this wear include the incorporation in the composition of agents having properties of toughening the film, such as silica.

It is thus found that, to date, it has proved to be particularly complicated to obtain a compromise between suppleness/flexibility of the film, on the one hand, and hardness of the film, on the other hand. It is this problem which forms the basis of the present invention.

This is because the inventor has been posed the problem of succeeding in producing a film exhibiting a degree of flexibility/suppleness, resulting in good resistance to chipping, while being sufficiently hard to moderate the wearing thereof in the case of rubbing movements.

Thus, a subject-matter of the present invention is a polymer with a "star" structure represented by the following formula (I):

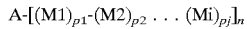

in which:
A represents a polyfunctional centre, with a functionality of "n", n being an integer greater than or equal to 2,
$[(M1)_{p1}\text{-}(M2)_{p2} \ldots (Mi)_{pj}]$ represents a polymer chain, also known as a "branch", composed of identical or different polymerized monomers Mi having a polymerization index pj, each branch being identical or different and being grafted covalently to the centre A;
being greater than or equal to 2 and pj being greater than or equal to 2;
the polymer comprising one or more monomers Mi chosen from polymerized monomers Mk, which may be identical or different, wherein a homopolymer formed by the corresponding polymerized monomers Mk has a Tg of greater than or equal to approximately 0° C., preferably of greater than or equal to 5° C. and even better still of greater than or equal to 10° C.; this or these monomers Mi being present, in the final polymer, in an amount of approximately 55–98% by weight, preferably in an amount of 75–95% by weight and even better still in an amount of 80–90% by weight with respect to the total weight of monomers; and
the polymer furthermore comprising one or more monomers Mj chosen from polymerized monomers Mj, which may be identical or different, wherein a homopolymer formed by the corresponding polymerized monomers Mj has a Tg of less than or equal to approximately 0° C., preferably of less than or equal to –5° C. and even better still of less than or equal to –10° C.; this or these monomers Mj being present, in the final polymer, in an amount of approximately 2–45% by weight, preferably in an amount of 5–25% by weight and even better still in an amount of 10–20% by weight with respect to the total weight of monomers.

Another subject-matter of the invention is a composition comprising, in a physiologically acceptable medium, at least one polymer as defined above.

Another subject-matter of the invention is a process for the cosmetic treatment of the hair, eyelashes, eyebrows or nails, characterized in that it comprises applying, to the latter, a cosmetic composition as defined above.

Another subject-matter of the invention is the use of at least one polymer as above in a cosmetic composition or for the preparation of a pharmaceutical composition which makes it possible to obtain a film exhibiting good resistance to chipping, to impacts, to rubbing movements, to scratches and/or to pressing actions.

The inventor has found that, on using the polymers as claimed, a composition is obtained which is easy to apply and which results in a homogeneous film with excellent gloss.

Furthermore, the film obtained exhibits a longer lifetime, due to its improved resistance to attacks, such as impacts, rubbing movements, scratches or pressing actions.

The compositions according to the invention can be readily applied and spread easily, in particular over the nails. The compositions according to the invention especially find a particularly advantageous application in the field of making up or caring for keratinous fibres, such as the nails, whether natural or artificial, eyelashes, eyebrows and hair, including body hair.

The composition according to the invention therefore comprises a polymer, the "star" structure of which can be illustrated, in a general way, by the following formula (I):

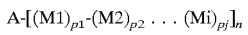

in which:
A represents a polyfunctional centre, with a functionality of "n", n being an integer greater than or equal to 2, preferably of between 4 and 10,
$[(M1)_{p1}\text{-}(M2)_{p2} \ldots (Mi)_{pj}]$ represents a polymeric chain, also known as a "branch", composed of identical or different polymerized monomers Mi having a polymerization index pj, each branch being identical or different and being grafted covalently to the centre A;

i being greater than or equal to 2, preferably of between 2 and 10; and pj being greater than or equal to 2, preferably of between 10 and 20,000.

The polymer chains are preferably provided in the form of blocks with a molecular mass of greater than or equal to 500 which can range up to 2,000,000.

In a preferred embodiment, the polymer used in the context of the present invention can be obtained by controlled radical polymerization, also known as "living" radical polymerization. This technique makes it possible in particular to overcome the limitations inherent in conventional radical polymerization, that is to say that it makes it possible in particular to control the length of the chains of the polymer which is formed and therefore to obtain block structures.

The controlled radical polymerization makes it possible to reduce the reactions in which the growing radical species is deactivated, in particular the termination stage, which reactions, in conventional radical polymerization, interrupt the growth of the polymer chain in an irreversible and uncontrolled way.

In order to decrease the probability of termination reactions, provision has been made to block, in a temporary and reversible way, the growing radical species by forming so-called "dormant" active species with the aid of a bond of low dissociation energy.

In particular, mention may be made of the possibility of using bonds of C—ONR type (by reaction with a nitroxyl); this is illustrated in particular by the article "Synthesis of nitroxy-functionalized polybutadiene by anionic polymerization using a nitroxy-functionalized terminator", published in Macromolecules, 1997, volume 30, pp. 4238–4242.

Mention may also be made of the possibility of using bonds of C-halide type (in the presence of metal/ligand complex). This is then described as atom transfer radical polymerization, also known under the abbreviation ATRP. This type of polymerization is reflected in control of the mass of the polymers which are formed and in a low polydispersity index by weight of the chains.

Atom transfer radical polymerization is generally carried out by polymerization:

of one or more radically polymerizable monomers, in the presence of an initiator having at least one radically transferable atom or group, of a compound comprising a transition metal capable of participating in a reduction stage with the initiator and a "dormant" polymer chain, and of a ligand, which can be chosen from compounds comprising a nitrogen (N), oxygen (O), phosphorus (P) or sulphur (S) atom, which compounds are capable of coordinating via a σ bond to the compound comprising a transition metal, or from compounds comprising a carbon atom, which compounds are capable of coordinating via a π or σ bond to the compound comprising a transition metal, the formation of direct bonds between the compound comprising a transition metal and the polymer in the course of formation being avoided.

This process is illustrated in particular in Application WO97/18247, the teaching of which can be drawn upon by a person skilled in the art in preparing the polymers coming within the scope of the present invention.

The nature and the amount of the monomers, initiator(s), compound(s) comprising the transition metal and ligand(s) will be chosen by a person skilled in the art on the basis of his overall knowledge, according to the result desired.

In particular, the monomers "M" (Mi, Mk, and Mj) can be chosen, alone or as a mixture, from radically polymerizable compounds comprising ethylenic unsaturation corresponding to the formula:

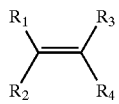

in which $R_1$, $R_2$, $R_3$ and $R_4$ are, independently of one another, chosen from:

a hydrogen atom;

a halogen atom;

a linear or branched alkyl radical having 1 to 20, preferably 1–6, more preferably 1–4, carbon atoms which is optionally substituted by one or more halogens and/or one or more —OH radicals;

a linear or branched alkenyl or alkynyl radical having 2 to 10, preferably 2–6, more preferably 2–4, carbon atoms which is optionally substituted by one or more halogens;

a cyclic hydrocarbonaceous (cycloalkyl) radical having 3 to 8 carbon atoms which is optionally substituted by one or more halogen, nitrogen, sulphur or oxygen atoms;

a radical chosen from CN, $C(=Y)R^5$, $C(=Y)NR^6R^7$, $YC(=Y)R^5$, cyclic $NC(=Y)R^5$, $SOR^5$, $SO_2R^5$, $OSO_2R^5$, $NR^8SO_2R^5$, $PR^5_2$, $P(=Y)R^5_2$, $YPR^5_2$, which $YP(=Y)R^5_2$, $NR^2_2$, can be quaternized with an additional $R^8$ group, aryl and heterocyclyl, with:

Y represents O, S or $NR^8$ (preferably O), $R^5$ represents a linear or branched alkyl, alkylthio or alkoxy radical having 1–20 carbon atoms; an OH radical; an OM' radical with M'=alkali metal; an aryloxy radical or a heterocyclyloxy radical;

$R^6$ and $R^7$ represent, independently of one another, H or a linear or branched alkyl radical having 1–20 carbon atoms; it being given that $R^6$ and $R^7$ can be joined to form an alkylene group having 2–7, preferably 2–5, carbon atoms;

$R^8$ represents H, a linear or branched alkyl radical having 1–20 carbon atoms or an aryl radical;

a —COOR radical, in which R is a linear or branched alkyl radical having 1 to 20, preferably 1–6, carbon atoms which is optionally substituted by one or more halogens;

a —CONHR' radical, in which R' is hydrogen or a saturated or unsaturated, linear or branched, hydrocarbonaceous radical having 1 to 20, preferably 1–6, carbon atoms which is optionally substituted by one or more halogens, nitrogens and/or oxygens;

an —OCOR" radical, in which R" is hydrogen or a saturated or unsaturated, linear or branched, hydrocarbonaceous radical having 1 to 20 carbon atoms which is optionally substituted by one or more halogens, nitrogens and/or oxygens;

a radical comprising at least one silicon atom and in particular radicals such as: an —R-siloxane radical, a —CONHR-siloxane radical, a —COOR-siloxane radical or an —OCO—R-siloxane radical, in which radicals R is a linear or branched alkyl, alkylthio, alkoxy, aryloxy or heterocycloxy radical having 1–20 carbon atoms.

The term "siloxane" is understood to mean a compound comprising $(-SiR^aR^bO-)_n$ units, in which units $R^a$ and $R^b$ can represent, independently of one another, a hydrogen; a halogen; a saturated or unsaturated, linear or branched, hydrocarbonaceous radical having 1 to 36 carbon atoms which is optionally substituted by one or more halogens, nitrogens and/or oxygens; or a cyclic hydrocarbonaceous radical having 1 to 20 carbon atoms; n being greater than or equal to 1.

For the purpose of this invention, the term "independent," when used to describe the relationship of radicals, atoms, substituents, functional groups, etc., means that each of the radicals, atoms, substituents, functional groups, etc. may be the same or different from the other, or some radicals, atoms, substituents, functional groups, etc., may be the same while the others may be different.

Mention may in particular be made of polydimethylsiloxanes (PDMSs) comprising 1 to 200, preferably less than 100, repeat units.

Furthermore, $R^1$ and $R^3$ can be connected to one another so as to form a ring of formula $(CH_2)_n$ which can be substituted by one or more halogens and/or oxygens and/or nitrogens and/or by alkyl radicals having 1 to 6 carbon atoms.

The term "aryl" or "heterocyclyl" is understood to mean the definition commonly understood by a person skilled in the art and which may be illustrated by the prior art WO97/18247.

Preferably, the monomers M can be chosen from:
acrylic or methacrylic esters obtained from linear, branched or cyclic aliphatic alcohols and/or from aromatic alcohols, preferably $C_1$–$C_{20}$ alcohols, such as methyl(meth)acrylate, ethyl(meth)acrylate, propyl (meth)acrylate, butyl(meth)acrylate, isobutyl(meth)acrylate or tert-butyl(meth)acrylate;

$C_1$–$C_4$ hydroxyalkyl(meth)acrylates, such as 2-hydroxyethyl(meth)acrylate or 2-hydroxypropyl (meth)acrylate;

ethylene glycol, diethylene glycol or polyethylene glycol (meth)acrylates with a hydroxyl or ether end;

vinyl, allyl or methallyl esters obtained from linear or branched $C_1$–$C_{10}$ or cyclic $C_1$–$C_6$ aliphatic alcohols and/or from aromatic alcohols, preferably $C_1$–$C_6$ alcohols, such as vinyl acetate, vinyl propionate, vinyl benzoate or vinyl tert-butylbenzoate;

N-vinylpyrrolidone; vinylcaprolactam; vinyl-N-alkylpyrroles having 1 to 6 carbon atoms; vinyloxazoles; vinylthiazoles; vinylpyrimidines; vinylimidazoles; and vinyl ketones;

(meth)acrylamides obtained from linear, branched or cyclic aliphatic amines and/or from aromatic amines, preferably $C_1$–$C_{20}$ amines, such as tert-butylacrylamide; and (meth)acrylamides, such as acrylamide, methacrylamide or di($C_1$–$C_4$)alkyl(meth) acrylamides;

olefins, such as ethylene, propylene, styrene or substituted styrene;

fluorinated or perfluorinated acrylic or vinyl monomers, in particular (meth)acrylic esters with perfluoroalkyl units;

monomers comprising an amine functional group in the free or else partially or completely neutralized or else partially or completely quaternized form, such as dimethylaminoethyl(meth)acrylate, dimethylaminoethylmethacrylamide, vinylamine, vinylpyridine or diallyidimethylammonium chloride;

carboxybetaines or sulphobetaines obtained by partial or complete quaternization of monomers comprising ethylenic unsaturation comprising an amine functional group by sodium salts of carboxylic acids comprising a mobile halide (sodium chloroacetate, for example) or by cyclic sulphones (propane sulphone);

silicone-comprising (meth)acrylates or (meth) acrylamides, in particular (meth)acrylic esters comprising siloxane units;

their mixtures.

The particularly preferred monomers are chosen from:
(meth)acrylic esters obtained from linear or branched aliphatic alcohols, preferably $C_1$–$C_{20}$ alcohols;

$C_1$–$C_{20}$ (meth)acrylic esters comprising perfluoroalkyl units;

$C_1$–$C_{20}$ (meth)acrylic esters comprising siloxane units;

(meth)acrylamides obtained from linear, branched or cyclic aliphatic amines and/or from aromatic amines, preferably $C_1$–$C_{20}$ amines, such as tert-butylacrylamide; or (meth)acrylamides, such as acrylamide, methacrylamide or di($C_1$–$C_4$)alkyl(meth) acrylamides;

vinyl, allyl or methallyl esters obtained from linear or branched $C_1$–$C_{10}$ or cyclic $C_1$–$C_6$ aliphatic alcohols;

vinylcaprolactam;

optionally substituted styrene;

their mixtures.

In the context of the present invention, the initiator can be any compound, in particular a molecular or polymeric compound, having at least two atoms and/or groups which are radically transferable by polymerization.

The initiator can in particular be an oligomer or a polymer capable of being obtained by radical polymerization, by polycondensation, by anionic or cationic polymerization or by ring opening.

The transferable atoms and/or groups can be situated at the ends of the polymer chain or along the backbone.

Mention may in particular be made of the compounds corresponding to one of the following formulae:

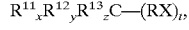

in which x, y and z represent an integer ranging from 0 to 4, t an integer ranging from 1 to 4, and x+y+z=4–t;

$R^{13}{}_xC_6$—$(RX)_y$ (saturated ring with 6 carbons), in which x represents an integer ranging from 7 to 11, y represents an integer ranging from 1 to 5, and x+y=12;

$R^{13}{}_xXC_6$—$(RX)_y$ (unsaturated ring with 6 carbons), in which x represents an integer ranging from 0 to 5, y represents an integer ranging from 1 to 6, and x+y=6;

—[—($R^{11}$)($R^{12}$)($R^{13}$)C—(RX)—]$_n$, in which n is greater than or equal to 1; cyclic or linear;

—[—($R^{12}$)$_x$C$_6$(RX)$_y$—$R^{11}$—]$_n$, in which x represents an integer ranging from 0 to 6, y represents an integer ranging from 1 to 6 and n is greater than or equal to 1, with x+y=4 or 6; cyclic or linear;

—[—($R^{12}$)$_x$C$_6$(RX)$_y$—$R^{11}$—]$_n$, in which x represents an integer ranging from 0 to 12, y represents an integer ranging from 1 to 12 and n is greater than or equal to 1, with x+y=10 or 12; cyclic or linear;

$R^{11}R^{12}R^{13}Si-X$

—[OSi($R^{11}$)$_x$(RX)$_y$]$_n$, cyclic or linear, in which x and y represent an integer ranging from 0 to 2 and n is greater than or equal to 1, with x+y=2;

$R^{11}R^{12}N-X$ $R^{11}N-X_2$ ($R^{11}$)$_x$P(O)$_y$—X$_{3-x}$, in which x and y represent integers ranging from 0 to 2 and x+y=5;

($R^{11}$O)$_x$P(O)$_y$—X$_{3-x}$, in which x and y represent integers ranging from 0 to 2 and x+y=5;

[($R^{11}$)$_t$N$_z$P(O)$_x$(O—RX)$_y$—]$_n$, cyclic or linear, in which x represents an integer ranging from 0 to 4, y represents an integer ranging from 1 to 5, z represents an integer ranging from 0 to 2, t represents an integer ranging from 0 to 3 and n is greater than or equal to 1;

in which:

R, $R^{11}$, $R^{12}$ and $R^{13}$ represent, independently of one another, a hydrogen or halogen atom; a linear or branched alkyl radical having 1–20, preferably 1–10 and more preferably 1–6 carbon atoms; a cycloalkyl radical having 3–8 carbon atoms; a —C(=Y)$R^5$, —C(=Y)NR$^6$R$^7$ or —R$^8_3$Si radical (see the definitions of $R^5$ to $R^8$ above);

—COCl; —OH; —CN; an alkenyl or alkynyl radical having 2–20, preferably 2–6, carbon atoms; an oxiranyl or glycidyl radical or an alkylene or alkenylene radical substituted with an oxiranyl or a glycidyl; an aryl, heterocyclyl, aralkyl or aralkenyl radical; or an alkyl radical having 1–6 carbon atoms in which all or part of the hydrogen atoms are substituted either by halogen atoms, such as fluorine, chlorine or bromine, or by an alkoxy group having 1–4 carbon atoms or by an aryl, heterocyclyl, —C(=Y)$R^5$, —C(=Y)NR$^6$R$^7$, oxiranyl or glycidyl radical;

X represents a halogen atom, such as Cl, Br or I, or an —OR', —SR, —SeR, —OC(=O)R', —OP(=O)R', —OP(=O)(OR')$_2$, —OP(=O)OR', —O—NR'$_2$, —S—C(=S)NR'$_2$, —CN, —NC, —SCN, —CNS, —OCN, —CNO and —N$_3$ radical, in which R' represents an alkyl radical having 1–20 carbon atoms which is optionally substituted by one or more halogen atoms, in particular fluorine and/or chlorine atoms, and R represents a linear or branched alkyl or aryl radical having 1–20, preferably 1–10, carbon atoms, it additionally being possible for the —NR'$_2$ group to represent a cyclic group, the two R' groups being joined so as to form a 5-, 6- or 7-membered heterocycle.

Preferably, X represents a halogen atom and in particular a chlorine or bromine atom.

The initiator is preferably chosen from the compounds of formula $R^{13}_xC_6$—(RX)$_y$ (saturated ring with 6 carbons) in which x represents an integer ranging from 7 to 11, y represents an integer ranging from 1 to 5 and x+y=12;

—[—($R^{12}$)$_x$C$_6$(RX)$_y$—$R^{11}$—]$_n$, in which x represent an integer ranging from 0 to 6, y represents an integer ranging from 1 to 6 and n is greater than or equal to 1, with x+y=4 or 6; cyclic or linear; and —[OSi($R^{11}$)$_x$(RX)$_y$]$_n$, cyclic or linear, in which x and y represent an integer ranging from 0 to 2 and n is greater than or equal to 1, with x+y=2.

Mention may in particular be made, as initiator, of the following compounds:

octa(2-isobutyrylbromide)octa(tert-butyl)calix(8)arene, octa(2-propionylbromide)octa(tert-butyl)calix(8)arene, and hexakis(α-bromomethyl)benzene.

The compound comprising a transition metal which is capable of participating in a reduction stage with the initiator and a "dormant" polymer chain can be chosen from those which correspond to the formula $M^{n+}X'_n$, in which formula:

M can be chosen from Cu, Au, Ag, Hg, Ni, Pd, Pt, Rh, Co, Ir, Fe, Ru, Os, Re, Mn, Cr, Mo, W, V, Nb, Ta and Zn, X' can represent a halogen (in particular bromine or chlorine), OH, (O)$_{1/2}$, an alkoxy radical having 1–6 carbon atoms, (SO$_4$)$_{1/2}$, (PO$_4$)$_{1/3}$, (HPO$_4$)$_{1/2}$, (H$_2$PO$_4$), a triflate, hexafluorophosphate, methanesulphonate, arylsulphonate, SeR, CN, NC, SCN, CNS, OCN, CNO, N$_3$ and R'CO$_2$ radical, in which R represents a linear or branched alkyl or aryl radical having 1–20, preferably 1–10, carbon atoms and R' represents H or a linear or branched alkyl radical having 1–6 carbon atoms or an aryl radical which is optionally substituted by one or more halogen atoms, in particular fluorine and/or chlorine atoms;

n is the charge on the metal.

The choice is preferably made of M representing copper or ruthenium and X' representing bromine or chlorine.

Mention may in particular be made of copper bromide.

Mention may be made, among the ligands capable of being used in the context of the present invention, of compounds comprising at least one nitrogen, oxygen, phosphorus and/or sulphur atom which are capable of coordinating via a σ bond to the compound comprising a transition metal.

Mention may also be made of compounds comprising at least two carbon atoms which are capable of coordinating via a π bond to the compound comprising a transition metal.

Mention may further be made of compounds comprising at least one carbon atom which are capable of coordinating via a σ bond to the compound comprising a transition metal but which do not form a carbon-carbon bond with the monomer during the polymerization, that is to say which do not participate in β-addition reactions with the monomers.

Mention may further be made of compounds capable of coordinating via μ or η bond to the compound comprising a transition metal.

Mention may in particular be made of the compounds of formula:

$$R^9-Z-(R^{14}-Z)_m-R^{10}$$

in which:

$R^9$ and $R^{10}$ are, independently of one another, a hydrogen atom; a linear or branched alkyl radical having 1–20, preferably 1–10, carbon atoms; an aryl radical; a heterocyclyl radical; or an alkyl radical having 1–6 carbon atoms which is substituted with an alkoxy radical having 1–6 carbon atoms or a dialkylamino radical having 1–4 carbon atoms or a —C(=Y)$R^5$ or —C(=Y)NR$^6$R$^7$ and/or YC(=Y)$R^8$ radical (see the definitions $R^5$ to $R^8$ and Y above);

it being given that $R^9$ and $R^{10}$ can be joined so as to form a saturated or unsaturated ring;

$R^{14}$ represents, independently of one another, a divalent group chosen from alkanediyls having 2–4 carbon atoms; alkenylenes having 2–4 carbon atoms; cycloalkanediyls having 3–8 carbon atoms; cycloalkenediyls having 3–8 carbon atoms; arenediyls and heterocyclylenes;

Z represents O, S, NR$^{15}$ or PR$^{15}$, with R$^{15}$ representing H; a linear or branched alkyl radical having 1–20 carbon atoms; an aryl radical; a heterocyclyl radical; or an alkyl radical having 1–6 carbon atoms which is substituted with an alkoxy radical having 1–6 carbon atoms or a dialkylamino radical having 1–4 carbon atoms or a $—C(=Y)R^5$ or $—C(=Y)NR^6R^7$ and/or $YC(=Y)R^8$ radical (see the definitions of $R^5$ to $R^8$ and Y above);

m is between 0 and 6.

Mention may also be made of the compounds of formula: $R^{20}R^{21}C[C(=Y)R^5]$ in which:

$R^{20}$ and $R^{21}$ are, independently of one another, a hydrogen atom; a halogen atom; a linear or branched alkyl radical having 1–20, preferably 1–10, carbon atoms; an aryl radical; or a heterocyclyl radical; it being given that $R^{20}$ and $R^{21}$ can be joined so as to form a saturated or unsaturated ring; it being given that, in addition, each radical can be substituted with an alkyl radical having 1–6 carbon atoms, an alkoxy radical having 1–6 carbon atoms or an aryl radical;

$R^5$ and Y being defined above.

Mention may further be made, as ligands, of carbon monoxide; optionally substituted porphyrins and porphycenes; optionally substituted ethylenediamine and propylenediamine; polyamines with tertiary amines, such as pentamethyidiethylenetriamine; aminoalcohols, such as aminoethanol and aminopropanol, which are optionally substituted; glycols, such as ethylene glycol or propylene glycol, which are optionally substituted; arenes, such as benzene, which are optionally substituted; optionally substituted cyclopentadiene; optionally substituted pyridines and bipyridines.

The polymerization of the monomers, in the presence of the initiator, of the compound comprising a transition metal and of the ligand which acts as activator, results in the production of a polymer having a star structure, which can be represented by the formula (I) given above, in which the monomers have polymerized to give "n" alike or different polymer chains all connected to a polyfunctional centre A which derives from the initiator.

It has been found that, in order to achieve the goal pursued by the present invention, that is to say to obtain a composition which does not exhibit the disadvantages of the prior art and which is in particular supple and flexible while being hard, which is thus resistant both to chipping and to rubbing, it is preferable to choose a polymer corresponding to the following criteria:

it preferably comprises one or more monomers Mk, the corresponding homopolymer of which exhibits a Tg of greater than or equal to approximately 0° C., preferably of greater than or equal to 5° C. and even better still of greater than or equal to 10° C.;

this or these monomers Mk being present in the final polymer in an amount of approximately 55–98% by weight, preferably in an amount of 75–95% by weight and even better still in an amount of 80–90% by weight with respect to the total weight of monomers; and the polymer preferably furthermore comprises one or more monomers Mj, the corresponding homopolymer of which exhibits a Tg of less than or equal to approximately 0° C., preferably of less than or equal to –5° C. and even better still of less than or equal to –10° C., this or these monomers Mj being present in the final polymer in an amount of approximately 2–45% by weight, preferably in an amount of 5–25% by weight and even better still in an amount of 10–20% by weight with respect to the total weight of monomers.

The Tg (glass transition temperature) is measured by DSC (Differential Scanning Calorimetry) according to ASTM Standard D3418-97.

It is thus possible to obtain small soft nodules, from the monomers Mj, which will be present inside a film-forming polymeric matrix, obtained from the monomers Mi.

Furthermore, in a preferred embodiment of the invention, at least one of the monomers Mi or Mj comprises hydrophilic units, such as acid, alcohol, amine and/or amide units, which makes it possible to further improve the adhesion of the polymer to the substrate.

The polymers as defined in the present invention preferably are be film-forming or can be rendered film-forming by addition of an additional agent which is able to form a film. The term "film-forming" is understood to mean that the polymer, after application to a substrate and evaporation of the solvent (aqueous or organic), results in a transparent and uncracked film.

Such an additional agent which is able to form a film can be chosen from any compound known to a person skilled in the art as being capable of fulfilling the desired role and can be chosen in particular from plasticizing agents and/or from coalescence agents. Mention may in particular be made, alone or as a mixture, of:

glycols and their derivatives, such as diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether;

glycerol esters, such as glycerol diacetate (diacetin) and glycerol triacetate (triacetin);

propylene glycol derivatives, in particular propylene glycol phenyl ether, propylene glycol diacetate, propylene glycol methyl ether, propylene glycol ethyl ether, propylene glycol butyl ether, dipropylene glycol methyl ether, dipropylene glycol butyl ether, dipropylene glycol ethyl ether, tripropylene glycol butyl ether or tripropylene glycol methyl ether;

acid esters, in particular carboxylic acid esters, such as citrates, phthalates, adipates, carbonates, tartrates, phosphates or sebacates, oxyethylenated derivatives, such as oxyethylenated oils, in particular vegetable oils, such as castor oil; or oxyethylenated silicone oils.

The amount of additional agent which is able to form a film can be chosen by a person skilled in the art on the basis of his overall knowledge so as to form a film having the desired mechanical properties while retaining, in the composition, cosmetically acceptable properties.

In a preferred embodiment of the invention, a polymer, optionally in combination with additional agents which are able to form a film, is chosen which makes it possible to obtain a film having a surface hardness of less than 110, preferably of between 1 and 70 and even better still of between 5 and 55.

The hardness measurement method is described before the examples.

The polymers as defined above can be present in the medium in a form dissolved or dispersed in an aqueous, organic or aqueous/organic phase, in particular an alcoholic or aqueous/alcoholic phase, and/or a fatty phase, according to the application envisaged.

The polymers can be present in the composition according to the invention in an amount which can be easily determined by a person skilled in the art according to the application envisaged and which can be between 1 and 60% by weight, on a dry basis, with respect to the total weight of the composition, preferably between 1 and 50% by weight and preferably between 5 and 40% by weight.

The cosmetic or pharmaceutical compositions according to the invention therefore additionally comprise a cosmetically or pharmaceutically acceptable medium which can be chosen by a person skilled in the art according to the application envisaged.

This medium can comprise an aqueous phase, a fatty phase and/or an organic phase.

The aqueous phase can comprise water and/or a thermal water and/or a spring water and/or a mineral water and/or a floral water.

It can also comprise one or more cosmetically acceptable organic solvents or else a mixture of water and of one or more cosmetically acceptable organic solvents. Mention may be made, among these organic solvents, of:

- alcohols which are liquid at 25° C., in particular $C_1$–$C_4$ alcohols, such as ethanol, isopropanol, n-propanol, diacetone alcohol, 2-butoxyethanol or cyclohexanol;
- ketones which are liquid at 25° C., such as methyl ethyl ketone, methyl isobutyl ketone, diisobutyl ketone, isophorone, cyclohexanone or acetone;
- lower $C_1$–$C_8$ carboxylic acid esters, such as methyl acetate, ethyl acetate, propyl acetate, n-butyl acetate or isopentyl acetate;
- ethers which are liquid at 25° C., such as diethyl ether, dimethyl ether or dichlorodiethyl ether;
- alcanes which are liquid at 25° C., such as decane, heptane, dodecane or cyclohexane;
- cyclic aromatic compounds which are liquid at 25° C., such as toluene and xylene;
- aldehydes which are liquid at 25° C., such as benzaldehyde or acetaldehyde;
- their mixtures.

The composition may additionally comprise a fatty phase which can comprise conventional volatile or non-volatile oils, gums and/or waxes of animal, vegetable, mineral or synthetic origin, alone or as mixtures, in particular:

- linear, branched or cyclic, volatile or non-volatile, silicone oils which are optionally organomodified; phenylated silicones; or silicone resins and gums which are liquid at room temperature;
- mineral oils, such as liquid paraffin and liquid petrolatum;
- oils of animal origin, such as perhydrosqualene or lanolin;
- oils of vegetable origin, such as liquid triglycerides, for example sunflower, maize, soybean, jojoba, gourd, grape seed, sesame, hazlenut, apricot, macadamia, avocado, sweet almond or castor oils, triglycerides of caprylic/capric acids, olive oil, groundnut oil, rapeseed oil or coconut oil;
- synthetic oils, such as purcellin oil, isoparaffins, fatty alcohols or esters of fatty acids;
- fluorinated and perfluorinated oils or fluorinated silicone oils;
- waxes chosen from known animal, fossil, vegetable, mineral or synthetic waxes, such as paraffin waxes, polyethylene waxes, carnauba or candelilla waxes, beeswaxes, lanolin wax, Chinese insect waxes, rice wax, ouricury wax, esparto wax, cork fibre wax, sugarcane wax, japan wax, sumach wax, montan wax, microcrystalline waxes, ozokerite, the waxes obtained by the Fischer-Tropsch synthesis, silicone waxes or their mixtures.

A person skilled in the art will know how to determine the nature and the amount of each of the constituents according to the application envisaged. By way of indication, when the composition comprises an organic solvent medium, the organic solvent can be present in a content of 25 to 95% by weight with respect to the total weight of the composition, preferably of 60–90% by weight.

The composition can additionally comprise at least one water-soluble dye and/or at least one pigment which are used conventionally in the field of cosmetics and make-up. The term "pigments" should be understood as meaning white or coloured and inorganic or organic particles which are insoluble in the medium and it which are intended to colour and/or opacify the composition. The pigments can be present in the composition in a proportion of 0–20% by weight of the final composition and preferably in a proportion of 1–5%. They can be white or coloured, inorganic and/or organic and conventional or nanometric in size. Mention may be made, among inorganic pigments and nanopigments, of titanium, zirconium or cerium oxides, as well as zinc, iron or chromium oxides or ferric blue. Mention may be made, among organic pigments, of carbon black and barium, strontium, calcium or aluminium lakes. Mention may be made, among water-soluble dyes, of the dyes which are standard in the field under consideration, such as the disodium salt of ponceau, the disodium salt of alizarine, quinoline yellow, the trisodium salt of amaranth, the disodium salt of tartrazine, the monosodium salt of rhodamine, the disodium salt of fuchsine or xanthophyll.

Furthermore, the composition according to the invention can comprise adjuvants commonly used in cosmetic or pharmaceutical compositions, such as:

- cosmetic and/or pharmaceutical active principles, such as softeners, antioxidants, opacifiers, emollients, hydroxy acids, antifoaming agents, moisturizers, vitamins, fragrances, preservatives, sequestering agents, UV screening agents, ceramides, agents for combating free radicals, complexing agents, odour absorbers, care active principles, agents for combating hair loss, antifungal or antiseptic agents, or antibacterials;
- fillers, pearlescent agents, lakes, thickeners, gelling agents, polymers, in particular fixing or conditioning polymers, propellants, basifying or acidifying agents, plasticizers, surfactants, spreading agents, wetting agents or dispersants;
- additional hydrophilic polymers, such as poly(vinyl alcohol)s and their copolymers, polysaccharides or cellulose polymers, or natural proteins or synthetic polypeptides;
- water-soluble polymers;
- other film-forming polymers, such as alkyd, acrylic and/or vinyl resins, polyurethanes and polyesters, celluloses and cellulose derivatives, such as nitrocellulose, and the resins resulting from the condensation of formaldehyde with an arylsulphonamide; film-forming polymers in aqueous dispersion, such as polyurethanes, polyester-polyurethanes, polyether-polyurethanes, radical polymers, in particular of acrylic, acrylic-styrene and/or vinyl type, polyesters or alkyd resins; or their mixtures.

Of course, a person skilled in the art will take care to choose this or these optional adjuvants and/or their amounts so that the advantageous properties of the composition according to the invention are not, or not substantially, detrimentally affected by the envisaged addition.

The compositions according to the invention can be provided in various forms and in particular in the form of oil-in-water or water-in-oil emulsions; of aqueous or oily dispersions or of dispersions in a solvent medium; of aqueous or oily solutions or of solutions in a solvent medium; in thickened or gelled fluid form, semi-solid form or soft paste form; or in solid form, such as a stick or tube.

They are preferably provided in the form of aqueous solutions or dispersions or of solutions or dispersions in an organic solvent medium which are optionally thickened.

The compositions according to the invention find an application in a large number of cosmetic or pharmaceutical treatments of the skin, hair, eyelashes, eyebrows, nails, mucous membranes or scalp.

They find a very specific application as make-up or care product for keratinous fibres and in particular the nails, whether natural or artificial, eyelashes, eyebrows or hair, including body hair.

They can be provided in particular in the form of a nail care base, of a nail varnish, of a mascara for the eyelashes and/or eyebrows, of a mascara for the hair or of a hair care or styling composition.

The invention is illustrated in more detail in the following examples.

A) Measurement of the Hardness

The hardness of the film is measured according to ASTM Standard D-43-66 or NF-T Standard 30-016 (October 1981) using a Persoz pendulum.

The film deposited on the substrate must have a thickness of approximately 300 microns before drying. After drying for 24 hours at 30° C. and under a relative humidity of 50%, a film is obtained which has a thickness of approximately 100 microns; its hardness is then measured at 30° C. and 50% relative humidity.

EXAMPLE 1

Preparation of the Initiator

The initiator prepared was 5,11,17,23,29,35,41,47-octa(2-propionylbromide)-49,50,51,52,53,54,55,56-octa(tert-butyl)calix(8)arene (M=2378 g).

The reactants used were as follows:

| | |
|---|---|
| 4-(tert-butyl)calix(8)arene (M = 1298 g), comprising 8 phenol units (Aldrich) | 15 g |
| 2-bromopropionyl bromide of formula $CH_3$—CHBr—COBr | 59.9 g |
| triethylamine | 28 g |
| tetrahydrofuran (THF) | 120 g |

The 4-(t-butyl)calix(8)arene and the solvent THF were added to a round-bottomed flask equipped with a stirrer and a thermometer; the mixture was left stirring for 10 minutes at room temperature.

The triethylamine was subsequently added, which took approximately 15 minutes.

The 2-bromopropionyl bromide, dissolved beforehand in THF, was then added at a temperature of approximately 5° C., which took approximately 1 h 30.

The mixture was left stirring for at least 12 hours at 5° C. and then the temperature was allowed to gradually rise to room temperature.

The solution obtained was concentrated by evaporating the THF. A product was precipitated from a water/ice mixture, extraction was then carried out with ethyl ether and the extract was dried over magnesium sulphate.

The solution obtained was concentrated and a compound was precipitated from a methanol/ice (90/10) mixture in a compound/precipitant ratio of 1/5.

23 g of compound were obtained, i.e., a yield of 85%, which compound existed in the form of a powder.

Characterization was carried out by NMR/GC or HPLC. The compound obtained exhibited values in accordance with those expected.

EXAMPLE 2

Preparation of an 8-Branched Star Polymer, Each Branch of Which was a Block Copolymer 1) First Stage: Preparation of a Star Polymer with 8 Poly(tert-butyl Acrlate) Branches The reactants used were as follows:

| | |
|---|---|
| monomer 1: tert-butyl acrylate (Tg = 50° C.) | 100 g |
| monomer 2: isobutyl acrylate (Tg = −20° C.) | 20 g |
| initiator (prepared according to Example 1) (corresponding to $4 \times 10^{-3}$ mol of RBr) | 1.19 g |
| CuBr (corresponding to $4 \times 10^{-3}$ mol) | 0.57 g |
| Bipyridine (corresponding to $8 \times 10^{-3}$ mol) | 1.25 g |

The monomers were distilled beforehand.

The reactants, except the monomers, were mixed in a sealed and flame-treated reactor comprising a nitrogen inlet and then the monomer 1 was added.

The reactor was heated under nitrogen to approximately 120° C. and reaction was then allowed to take place at 120° C. for 4 hours, the nitrogen inlet being disconnected.

2) Second Stage: Formation of the Second Block at the End of Each Branch

The monomer 2 was then added and reaction was again allowed to take place at 120° C. for 4 hours.

After reaction, the reaction mixture was allowed to cool; a viscous green solution was obtained, which solution was dissolved in dichloromethane. The polymer solution was passed through neutral alumina and the clear solution obtained was precipitated from a methanol/water (80/20) mixture in a polymer/precipitant ratio of 1/5.

115 g of polymer were obtained, i.e., a yield of 96%, which polymer existed in the form of a viscous product.

This polymer was a star polymer with 8 poly(isobutyl acrylate) branches, each branch of which was a block copolymer: calix(poly(tert-butyl acrylate)-block-poly (isobutyl acrylate)).

Characterization was carried out by GC:THF linear polystyrene equivalent, light scattering detection: 350,000 g/mol (theoretical mass: approximately 240,000); polydispersity index: 1.6.

The polymer obtained exhibited values in accordance with those expected. The polymer was soluble in ethanol. Hardness: 50 s

EXAMPLE 3

Nail Varnish

A nail varnish composition was prepared comprising:

| | |
|---|---|
| polymer obtained according to Example 2 | 25% |
| pigments | q.s. |
| solvents (ethyl acetate/butyl acetate (90/10)) | q.s. for 100% |

The polymer was dissolved in the mixture of solvents. A varnish composition was obtained which spread easily and made it possible to obtain a glossy film of appropriate hardness.

What is claimed is:

1. A film-forming polymer having a star structure chosen from structures of formula (I):

$$A-[(M1)_{p1}-(M2)_{p2}\ldots(Mi)_{pj}]_n \quad (I)$$

in which:
A is chosen from polyfunctional centers having a functionality n;
$[(M1)_{p1}-(M2)_{p2}\ldots(Mi)_{pj}]$ represents a branch comprising at least one polymerized monomeric unit Mi having a polymerization index pj;
n is an integer greater than or equal to 2;
pj is greater than or equal to 2;
there are at least two branches, which may be identical or different; and
said at least two branches are grafted covalently to A;
wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 0° C.;
wherein said at least one polymerized monomeric unit Mi contained by at least one of said at least two branches is chosen from polymerized monomeric units Mj, which may be identical or different, wherein a homopolymer formed by the corresponding polymerized monomeric units Mj has a Tg of less than or equal to 0° C.;
wherein said at least one polymerized monomeric unit Mi chosen from polymerized monomeric units Mk is present in an amount ranging from 55 to 98 percent by weight relative to the total weight of the polymerized monomeric units Mi; and
wherein said at least one polymerized monomeric unit Mi chosen from polymerized monomeric units Mj is present in an amount ranging from 2 to 45 percent by weight relative to the total weight of the polymerized monomeric units Mi,
wherein said film-forming polymer forms a film having a hardness of less than 110.

2. A polymer according to claim 1, wherein said homopolymer formed by the corresponding polymerized monomeric units Mk has a Tg of greater than or equal to 5° C.

3. A polymer according to claim 2, wherein said Tg has a value of greater than or equal to 10° C.

4. A polymer according to claim 1, wherein said homopolymer formed by the corresponding polymerized monomeric units Mj has a Tg of less than or equal to −5° C.

5. A polymer according to claim 4, wherein said Tg has a value of less than or equal to −10° C.

6. A polymer according to claim 1, wherein said at least one polymerized monomeric unit Mi chosen from polymerized monomers Mk is present in an amount ranging from 75 to 95 percent by weight relative to the total weight of the polymerized monomeric units Mi.

7. A polymer according to claim 6, wherein said amount ranges from 80 to 90 percent.

8. A polymer according to claim 1, wherein said at least one polymerized monomeric unit Mi chosen from polymerized monomeric unit Mj is present in an amount ranging from 5 to 25 percent by weight relative to the total weight of the polymerized monomeric units Mi.

9. A polymer according to claim 8, wherein said amount ranges from 10 to 20 percent.

10. A polymer according to claim 1, wherein said at least one of said branches has a form of a block and a molecular mass ranging from 500 to 2,000,000 Daltons.

11. A polymer according to claim 1, wherein said polymerized monomeric units Mk and Mj are independently chosen from radically polymerizable compounds containing an ethylenic unsaturation having a formula:

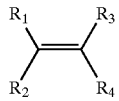

in which:
$R_1, R_2, R_3,$ and $R_4$ are, each independently of one another, chosen from:
a hydrogen atom;
halogen atoms;
linear and branched alkyl radicals having from 1 to 20 carbon atoms which are optionally substituted by at least one halogen atom or at least one —OH radical;
linear and branched alkenyl and alkynyl radicals having from 2 to 10 carbon atoms which are optionally substituted by at least one halogen atom;
cyclic hydrocarbonaceous radicals having from 3 to 8 carbon atoms which are optionally substituted by at least one halogen atom, nitrogen atom, sulphur atom, or oxygen atom;
radicals chosen from CN, $C(=Y)R^5$, $C(=Y)NR^6R^7$, $YC(=Y)R^5$, cyclic $NC(=Y)R^5$, $SOR^5$, $SO_2R^5$, $OSO_2R^5$, $NR^8SO_2R^5$, $PR^5{}_2$, $P(=Y)R^5{}_2$, $YPR^5{}_2$, $YP(=Y)R^5{}_2$, $NR^8{}_2$, $NR^8{}_3{}^+$, $NR^8{}_2(aryl)^+$, and $NR^8{}_2$(heterocycyl)$^+$,
in which:
Y is chosen from O, S, and $NR^8$;
$R^5$ is chosen from linear and branched alkyl radicals, alkylthio radicals, and alkoxy radicals having from 1 to 20 carbon atoms; an OH radical; OM' radicals in which M' is chosen from alkali metals; aryloxy radicals; and heterocyclyloxy radical;
$R^6$ and $R^7$, independently of one another, are chosen from a hydrogen atom, linear and branched alkyl radicals having from 1 to 20 carbon atoms; or $R^6$ and $R^7$ together form an alkylene group having from 2 to 7 carbon atoms;
$R^8$ is chosen from a hydrogen atom, linear and branched alkyl radicals having from 1 to 20 carbon atoms and an aryl radical;
COOR radicals, in which R is chosen from linear and branched alkyl radicals having from 1 to 20 carbon atoms which are optionally substituted by at least one halogen atom;
CONHR' radicals, in which R' is chosen from hydrogen atoms and saturated and unsaturated, linear and branched, hydrocarbonaceous radicals having from 1 to 20 carbon atoms which are optionally substituted by at least one halogen atom, nitrogen atom or oxygen atom;
OCOR" radicals, in which R" is chosen from hydrogen atoms and saturated and unsaturated, linear and branched, hydrocarbonaceous radicals having from 1 to 20 carbon atoms which are optionally substituted by at least one halogen atom, nitrogen atom, or oxygen atom; and
radicals comprising at least one silicon atom; or R¹ and R³ radicals together form a ring having the formula $(CH_2)_{n'}$ which can be substituted by at least one halogen atom, oxygen atom, nitrogen atom, or an alkyl radical having from 1 to 6 carbon atoms, in which n' is an integer ranging from 3 to 12.

12. A polymer according to claim 11, wherein at least one of $R_1$, $R_2$, $R_3$, and $R_4$, each independently of one another, is chosen from linear and branched alkyl radicals having from 1 to 6 carbon atoms which are optionally substituted by at least one halogen atom or at least one —OH radical.

13. A polymer according to claim 11, wherein at least one of $R_1$, $R_2$, $R_3$, and $R_4$, each independently of one another, is chosen from linear and branched alkyl radicals having from 1 to 4 carbon atoms which are optionally substituted by at least one halogen atom or at least one —OH radical.

14. A polymer according to claim 11, wherein at least one of $R_1$, $R_2$, $R_3$, and $R_4$, each independently of one another, is chosen from linear and branched alkenyl and alkynyl radicals having from 2 to 6 carbon atoms which are optionally substituted by at least one halogen atom.

15. A polymer according to claim 11, wherein at least one of $R_1$, $R_2$, $R_3$, and $R_4$, each independently of one another, are chosen from linear and branched alkenyl and alkynyl radicals having from 2 to 4 carbon atoms which are optionally substituted by at least one halogen atom.

16. A polymer according to claim 11, wherein at least one of $R_1$, $R_2$, $R_3$, and $R_4$, independently of one another, is chosen from $C(=Y)R^5$, $C(=Y)NR^6R^7$, $YC(=Y)R^5$, cyclic $NC(=Y)R^5$, $P(=Y)R^5_2$, $YPR^5_2$, and $YP(=Y)R^5_2$, in which Y is O.

17. A polymer according to claim 11, wherein at least one of $R_1$, $R_2$, $R_3$, and $R_4$, independently of one another, is chosen from $C(=Y)NR^6R^7$, in which $R^6$ and $R^7$ together form an alkylene group having from 2 to 5 carbon atoms.

18. A polymer according to claim 11, wherein at least one of $R_1$, $R_2$, $R_3$, and $R_4$, independently of one another, is chosen from COOR radicals, in which R is chosen from linear and branched alkyl radicals having from 1 to 6 carbon atoms which are optionally substituted by at least one halogen atom.

19. A polymer according to claim 11, wherein at least one of $R_1$, $R_2$, $R_3$, and $R_4$, independently of one another, is chosen from CONHR' radicals, in which R' is chosen from hydrogen atoms, saturated and unsaturated, linear and branched, hydrocarbonaceous radicals having from 1 to 6 carbon atoms which are optionally substituted by at least one halogen atom, nitrogen atom or oxygen atom.

20. A polymer according to claim 11, wherein at least one of $R_1$, $R_2$, $R_3$, and $R_4$, independently of one another, is chosen from radicals containing at least one silicon atom, wherein said radicals are chosen from —R-siloxane radicals, —CONHR-siloxane radicals, —COOR-siloxane radicals, and —OCO—R-siloxane radicals, in which R is chosen from linear and branched alkyl, alkylthio, alkoxy, aryloxy, and heterocycloxy radicals having from 1 to 20 carbon atoms.

21. A polymer according to claim 1, wherein said polymerized monomeric units Mj and Mk are independently chosen from:
   acrylic or methacrylic esters obtained from linear, branched, or cyclic aliphatic alcohols and/or from aromatic alcohols;
   $C_1$–$C_4$ hydroxyalkyl(meth)acrylates;
   ethylene glycol, diethylene glycol, and polyethylene glycol(meth)acrylates with a hydroxyl or ether end;
   vinyl, allyl, methallyl esters obtained from linear or branched $C_1$–$C_{10}$ aliphatic alcohols, cyclic $C_1$–$C_6$ aliphatic alcohols, and aromatic alcohols;
   N-vinylpyrrolidone; vinylcaprolactam; vinyl-N-alkylpyrroles having from 1 to 6 carbon atoms; vinyloxazoles; vinylthiazoles; vinylpyrimidines; vinylimidazoles; and vinyl ketones;
   (meth)acrylamides obtained from linear, branched, or cyclic aliphatic amines or from aromatic amines; (meth)acrylamides chosen from acrylamide, methacrylamide and di($C_1$–$C_4$)alkyl(meth)acrylamides;
   olefins;
   fluorinated or perfluorinated acrylic and vinyl monomers;
   monomers containing an amine functional group in the free or else partially or completely neutralized or else partially or completely quaternized form;
   carboxybetaines and sulphobetaines obtained by partial or complete quaternization of monomers containing at least one ethylenic unsaturation which contains an amine functional group, wherein said quaternization occurs by a sodium salt of a carboxylic acid which contains a mobile halide or by a cyclic sulphone; and
   silicone-containing (meth)acrylates and (meth)acrylamides.

22. A polymer according to claim 21, wherein said acrylic or methacrylic esters obtained from linear, branched, or cyclic aliphatic alcohols and/or from aromatic alcohols are obtained from $C_1$–$C_{20}$ alcohols.

23. A polymer according to claim 22, wherein said acrylic or methacrylic esters are chosen from methyl(meth)acrylates, ethyl(meth)acrylates, propyl(meth)acrylates, butyl(meth)acrylates, isobutyl(meth)acrylates, and tert-butyl(meth)acrylates.

24. A polymer according to claim 21, wherein said $C_1$–$C_4$ hydroxyalkyl(meth)acrylates are chosen from 2-hydroxyethyl(meth)acrylates and 2-hydroxypropyl(meth)acrylates.

25. A polymer according to claim 21, wherein said vinyl, allyl, and methallyl esters obtained from linear or branched $C_1$–$C_{10}$ aliphatic alcohols, cyclic $C_1$–$C_6$ aliphatic alcohols, and aromatic alcohols are obtained from $C_1$–$C_6$ alcohols.

26. A polymer according to claim 25, wherein said vinyl, allyl, and meth allyl esters are chosen from vinyl acetate, vinyl propionate, vinyl benzoate, and vinyl tertbutylbenzoate.

27. A polymer according to claim 21, wherein said (meth)acrylamides obtained from linear, branched, or cyclic aliphatic amines or from aromatic amines are obtained from $C_1$–$C_{20}$ amines.

28. A polymer according to claim 27, wherein said (meth)acrylamides are chosen from tert-butylacrylamide.

29. A polymer according to claim 21, wherein said olefins are chosen from ethylene, propylene, styrene, and substituted styrene.

30. A polymer according to claim 21, wherein said fluorinated or perfluorinated acrylic and vinyl monomers are chosen from (meth)acrylic esters containing at least one perfluoroalkyl unit.

31. A polymer according to claim 21, wherein said monomers containing an amine functional group in the free or else partially or completely neutralized or else partially or completely quaternized form are chosen from dimethylaminoethyl(meth)acrylate, dimethylaminoethylmethacrylamide, vinylamine, vinylpyridine, and diallyldimethylammonium chloride.

32. A polymer according to claim 21, wherein said carboxybetaines and sulphobetaines obtained by partial or complete quaternization of monomers containing at least one ethylenic unsaturation which contains an amine functional group by a sodium salt of a carboxylic acid which contains a mobile halide or by a cyclic sulphone.

33. A polymer according to claim 32, further wherein said sodium salt of the carboxylic acid is sodium chloroacetate.

34. A polymer according to claim 32, further wherein said cyclic sulphone is propane, sulphone.

35. A polymer according to claim 21, wherein said silicone-containing (meth)acrylates and (meth)acrylamides are chosen from (meth)acrylic esters containing at least one siloxane unit.

36. A polymer according to claim 1, wherein said polymerized monomeric units Mk and Mj are independently chosen from:
- (meth)acrylic esters obtained from linear or branched aliphatic alcohols;
- $C_1$–$C_{20}$ (meth)acrylic esters containing at least one perfluoroalkyl unit;
- $C_1$–$C_{20}$ (meth)acrylic esters containing at least one siloxane unit;
- (meth)acrylamides obtained from linear, branched, or cyclic aliphatic amines and/or from aromatic amines;
- (meth)acrylamides chosen from acrylamides, di($C_1$–$C_4$) alkyl(meth)acrylamides, and methacrylamides;
- vinyl, allyl, and methallyl esters obtained from linear or branched $C_1$–$C_{10}$ aliphatic alcohols and cyclic $C_1$–$C_6$ aliphatic alcohols;
- vinylcaprolactam; and
- styrene and substituted styrene.

37. A polymer according to claim 36, wherein said (meth)acrylic esters obtained from linear or branched aliphatic alcohols are obtained from $C_1$–$C_{20}$ alcohols.

38. A polymer according to claim 36, wherein said (meth)acrylamides are obtained from linear, branched, or cyclic aliphatic amines and/or from aromatic amines, and further wherein said aliphatic and/or aromatic amines are chosen from $C_1$–$C_{20}$ amines.

39. A polymer according to claim 36, wherein said (meth)acrylamides are chosen from tert-butylacrylamide.

40. A polymer according to claim 1, wherein at least one of said monomeric units Mk and Mj comprises at least one hydrophilic unit.

41. A polymer according to claim 40, wherein said at least one hydrophilic unit is chosen from acid units, alcohol units, and amide units.

42. A polymer according to claim 1, wherein said hardness ranges from 1 and 70.

43. A polymer according to claim 42, wherein the said hardness ranges from 5 to 55.

44. A composition, comprising, in a physiologically acceptable medium, at least one film-forming polymer having a star structure chosen from structures of formula (I):

A-[(M1)$_{p1}$-(M2)$_{p2}$ ... (Mi)$_{pj}$]$_n$ (I)

in which:
- A is chosen from polyfunctional centers having a functionality n;
- [(M1)$_{p1}$-(M2)$_{p2}$ ... (Mi)$_{pj}$] represents a branch comprising at least one polymerized monomeric unit Mi having a polymerization index pj;
- n is an integer greater than or equal to 2;
- pj is greater than or equal to 2;
- there are at least two branches, which may be identical or different; and
- said at least two branches are grafted covalently to A;

wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 0° C.; and wherein said at least one polymerized monomeric unit Mi contained by at least one of said at least two branches is chosen from polymerized monomeric units Mj, which may be identical or different, wherein a homopolymer formed by the corresponding polymerized monomeric units Mj has a Tg of less than or equal to 0° C., wherein said at least one film-forming polymer forms a film having a hardness of less than 110.

45. A composition according to claim 44, wherein said at least one polymerized monomeric unit Mi chosen from polymerized monomeric units Mk is present in an amount ranging from 55 to 98 percent by weight relative to the total weight of the polymerized monomeric units Mi.

46. A composition according to claim 44, wherein said at least one polymerized monomeric unit Mi chosen from polymerized monomeric units Mj is present in an amount ranging from 2 to 45 percent by weight relative to the total weight of the polymerized monomeric units Mi.

47. A composition according to claim 44, wherein said physiologically acceptable medium is chosen from pharmaceutically acceptable mediums and cosmetically acceptable mediums and further wherein said composition is chosen from forms of pharmaceutical compositions and cosmetic compositions.

48. A composition according to claim 44, further comprising at least one agent which is able to form a film.

49. A composition according to claim 48, wherein said at least one agent is chosen from plasticizing agents and coalescence agents.

50. A composition according to claim 44, wherein said at least one polymer is present in an amount ranging from 1 to 60 percent by weight, on a dry basis, with respect to the total weight of said composition.

51. A composition according to claim 50, wherein the range is from 1 to 50 percent by weight.

52. A composition according to claim 50, wherein the range is from 5 to 40 percent by weight.

53. A composition according to claim 44, wherein said at least one polymer is present in said physiologically acceptable medium containing at least one phase chosen from aqueous phases, organic phases, aqueous/organic phases, and fatty phases.

54. A composition according to claim 53, wherein said at least one phase is chosen from alcoholic and aqueous/alcoholic phases.

55. A composition according to claim 53, wherein said at least one polymer is dissolved or dispersed in said at least one phase.

56. A composition according to claim 44, wherein said composition has a form chosen from oil-in-water emulsions; water-in-oil emulsions; aqueous dispersions; oily dispersions; dispersions in a solvent medium; aqueous solutions; oily solutions; solutions in a solvent medium; thickened fluids; gelled fluids; semi-solids; soft paste forms; and solid forms.

57. A composition according to claim 56, wherein said solid forms are chosen from sticks and tubes.

58. A composition according to claim 44, wherein said composition has a form chosen from aqueous solutions, aqueous dispersions, and dispersions in an organic solvent medium.

59. A comparison according to claim 44, wherein said composition has a form chosen from make-up and care products for keratinous fibers.

60. A composition according to claim 59, wherein said keratinous fibers are chosen from nails, eyelashes, eyebrows, and hair.

61. A composition according to claim 60, wherein said nails are artificial.

62. A composition according to claim 60, wherein said hair is body hair.

63. A composition according to claim 44, wherein said composition has a form chosen from nail care bases, nail varnishes, mascaras for eyelashes and eyebrows, mascaras for the hair, and hair care and styling compositions.

64. A process for treating a keratinous substance, comprising applying to said keratinous substance a composition, comprising, in a physiologically acceptable medium, at least one film-forming polymer having a star structure chosen from structures of formula (I):

in which:

A is chosen from polyfunctional centers having a functionality n;

$[(M1)_{p1}\text{-}(M2)_{p2} \ldots (Mi)_{pj}]$ represents a branch comprising at least one polymerized monomeric unit Mi having a polymerization index pj;

n is an integer greater than or equal to 2;

pj is greater than or equal to 2;

there are at least two branches, which may be identical or different; and said at least two branches are grafted covalently to A;

wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 0° C.; and wherein said at least one polymerized monomeric unit Mi contained by at least one of said at least two branches is chosen from polymerized monomeric units Mj, which may be identical or different, wherein a homopolymer formed by the corresponding polymerized monomeric units Mj has a Tg of less than or equal to 0° C., wherein said at least one film-forming polymer forms a film having a hardness of less than 110.

65. A process according to claim 64, wherein said at least one polymerized monomeric unit Mi chosen from polymerized monomeric units Mk is present in an amount ranging from 55 to 98 percent by weight relative to the total weight of the polymerized monomeric units Mi.

66. A process according to claim 64, wherein said at least one polymerized monomeric unit Mi chosen from polymerized monomeric units Mj is present in an amount ranging from 2 to 45 percent by weight relative to the total weight of the polymerized monomeric units Mi.

67. A process according to claim 64, wherein said keratinous substance is chosen from hair, eyelashes, eyebrows, and nails.

68. A process according to claim 67, wherein said keratinous substance is chosen from human keratinous substances.

69. A process for preparing a cosmetic or pharmaceutical composition which is able to form a film, comprising introducing, in a physiologically acceptable medium, at least one film-forming polymer in an amount effective increasing resistance to chipping, impact, rubbing movement, scratches, or pressing action of said film to said cosmetic or pharmaceutical composition, wherein said at least one film-forming polymer having a star structure chosen from structures of formula (I):

in which:

A is chosen from polyfunctional centers having a functionality n;

$[(M1)_{p1}\text{-}(M2)_{p2} \ldots (Mi)_{pj}]$ represents a branch comprising at least one polymerized monomeric unit Mi having a polymerization index pj;

n is an integer greater than or equal to 2;

pj is greater than or equal to 2;

there are at least two branches, which may be identical or different; and said at least two branches are grafted covalently to A;

wherein said at least one polymerized monomeric unit Mi comprised by at least one of said at least two branches is chosen from polymerized monomeric units Mk, which may be identical or different, wherein a homopolymer formed by the corresponding polymerized monomeric units Mk has a Tg of greater than or equal to 0° C.; and wherein said at least one polymerized monomeric unit Mi contained by at least one of said at least two branches is chosen from polymerized monomeric unit Mj, which may be identical or different, wherein a homopolymer formed by the corresponding polymerized monomeric units Mj has a Tg of less than or equal to 0° C., wherein said at least one film-forming polymer forms a film having a hardness of less than 110.

70. A process according to claim 69, wherein said at least one polymerized monomeric unit Mi chosen from polymerized monomeric units Mk is present in an amount ranging from 55 to 98 percent by weight relative to the total weight of the polymerized monomeric units Mi.

71. A process according to claim 69, wherein said at least one polymerized monomeric unit Mi chosen from polymerized monomeric units Mj is present in an amount ranging from 2 to 45 percent by weight relative to the total weight of the polymerized monomeric units Mi.

* * * * *

UNITED STATES PATENT AND TRADEMARK OFFICE
CERTIFICATE OF CORRECTION

PATENT NO. : 6,552,146 B1 Page 1 of 1
DATED : April 22, 2003
INVENTOR(S) : Nathalie Mougin It is certified that error appears in the above-identified patent and that said Letters Patent is hereby corrected as shown below:

Column 17,
Line 5, "3to" should read -- 3 to --.

Column 18,
Line 41, "meth allyl" should read -- methallyl --.

Column 19,
Line 6, after "propane", delete the comma.

Column 21,
Line 1, "comparison" should read -- composition --.

Signed and Sealed this

First Day of July, 2003

JAMES E. ROGAN
*Director of the United States Patent and Trademark Office*